(12) United States Patent
Patzer

(10) Patent No.: US 6,983,274 B2
(45) Date of Patent: Jan. 3, 2006

(54) MULTIPLE ALIGNMENT GENOME SEQUENCE MATCHING PROCESSOR

(76) Inventor: Aaron Thomas Patzer, The Graduate College, 88 College Rd., West, Princeton, NJ (US) 08544

( * ) Notice: Subject to any disclaimer, the term of this patent is extended or adjusted under 35 U.S.C. 154(b) by 319 days.

(21) Appl. No.: 10/252,965

(22) Filed: Sep. 23, 2002

(65) Prior Publication Data

US 2004/0059721 A1 Mar. 25, 2004

(51) Int. Cl.
*G06F 17/60* (2006.01)

(52) U.S. Cl. ............................. 707/3; 707/4; 370/386; 370/462

(58) Field of Classification Search ...................... 707/2, 707/3, 4; 370/386, 462
See application file for complete search history.

(56) References Cited

U.S. PATENT DOCUMENTS

| | | | |
|---|---|---|---|
| 5,632,041 A | 5/1997 | Peterson | |
| 5,706,498 A | 1/1998 | Fujimiya | |
| 5,724,253 A | 3/1998 | Skovira | |
| 5,850,227 A | * 12/1998 | Longhenry et al. | ......... 345/671 |
| 5,883,895 A | * 3/1999 | Davis et al. | ................ 370/462 |
| 5,964,860 A | 10/1999 | Peterson | |

OTHER PUBLICATIONS

Richard Hughey. "Parallel Hardware for Sequence Comparison and Alignment." Comput. Applic. Biosci., 12, pp. 473–479 1996.

Aaron Patzer. "Highly Parallel DNA Sequence Matching and Alignment Processor." 5th IEEE DDECS Conf., Apr. 17–19, 2002. Brno, Czech Republic.

* cited by examiner

*Primary Examiner*—Charles Rones

(57) ABSTRACT

A digital hardware system slides a sequence to be searched, such as a genome, past a query sequence, such as a DNA fragment, via shift registers. In parallel, multiple alignments between search and query sequences are compared. As each alignment consists of many elements (characters), the parallel matching process is highly accelerated over sequential element-by-element comparison. Individual element comparisons are made using equivalence operators, such as XNOR logic gates. The results of individual element comparisons are then consolidated into a single signal: "hit" or "miss", indicating whether all the elements for the particular alignment under test matched or not. After comparison, the search sequence is shifted by a number of elements equal to the number of parallel alignments compared, and the process repeats. An additional shifting prefetch buffer increases memory efficiency by alleviating the need to fetch data every cycle.

11 Claims, 5 Drawing Sheets

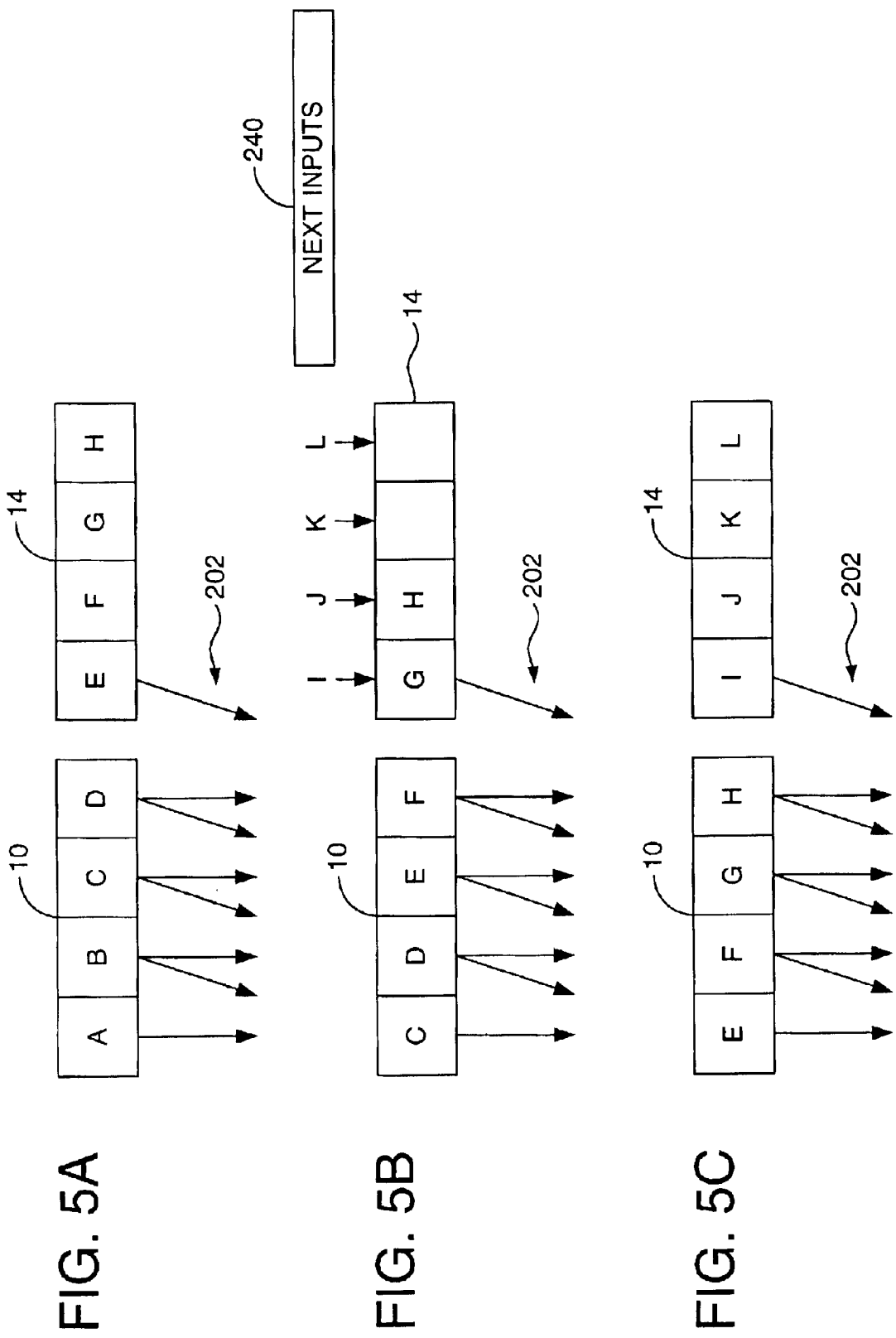

MULTIPLE ALIGNMENT GENOME SEQUENCE MATCHING PROCESSOR

BACKGROUND OF THE INVENTION

1. Field of the Invention

Figure 1:
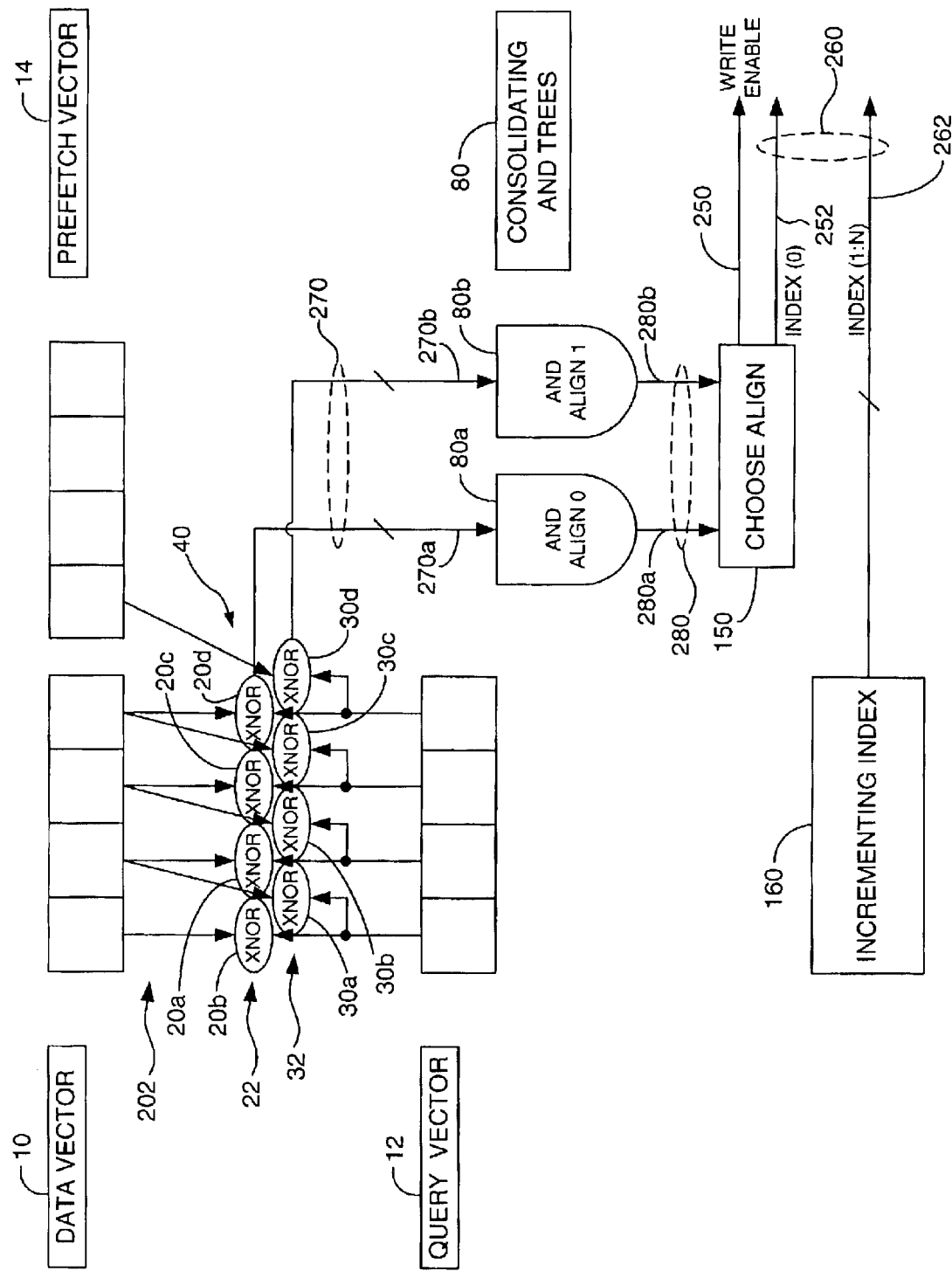

The invention relates generally to string matching techniques, specifically to a system and method for searching sequences, such as genomes, for a specified query, such as a DNA fragment.

2. Description of Prior and Related Art

The identification of sequence homology—a kind of match—between an unknown genetic test sample and a known genomic sequence often provides clues about the function, identity, or evolutionary relatedness of the sequence in question. This information can be used, for example, in determining genetic diseases, defects, and other hereditary characteristics. With the explosive rise in the amount of genetic data made possible by new sequencing technologies, the ability to screen newly discovered DNA sequences against large databases of known genes has become a particularly important—and computationally intensive—aspect of modern biology.

Another computationally and data intensive task of modern biology is sequence assembly: the process of reconstructing the original DNA sequence from the small DNA fragments output by sequencing equipment. DNA sequencing requires duplicating a target sequence and then randomly fracturing these duplicates. This random fracturing ensures that the subsequence fragments produced will contain enough overlapping information to facilitate sequence reconstruction. The subsequent chemical readout process requires these fragments to be at most 500 bases long to keep the error rate below 1%. The end result is a large number of DNA fragments. To assemble the original sequence after readout, each fragment—now represented digitally by characters A (Adenine), T (Thiamine), G (Guanine), and C (Cytosine)—is compared (matched) to all other fragments looking for a best fit overlap. Overlapping fragments are merged, and the process repeats until the entire sequence of the input strand has been determined.

This match and merger method takes considerable computational resources. Genomics companies for example, use supercomputing clusters for the task. Algorithmic analysis shows that full reassembly process is $\theta(N^2 \log_2 N)$ or higher, where N is the number of bases (nucleotides) in the DNA being sequenced. For a sequence the size of the human genome, full reconstruction through a pair-wise comparison of all reads has been estimated at several thousand years of compute-time on a general purpose computer, and therefore represents a formidable computational bottleneck.

Special purpose machines for accelerated genetic sequence analysis were first developed in the late 1980's when it was recognized that the growth of genetic databases outpaced Moore's law and the power of general purpose processors. With little exception, these machines have used a systolic array configuration consisting of hundreds to thousands of small processing elements, as this is the direct hardware adaptation of the dynamic programming algorithms used in biosequence analysis. These algorithms are typically based on a string edit distance optimization as first presented by Needleman and Wunsch ("A general method applicable to the search for similarities in the amino acid sequences of two proteins." J. Molecular Biology vol. 48, pgs. 443–453, 1970.), and later expanded and extended by Smith and Waterman ("Comparison of Biosequences". Adv. in Appl. Math. 2, pgs. 482–489, 1981.) The main variations between systolic architectures have involved trading ASIC speed for FPGA flexibility, using general purpose rather than specialized systolic arrays, and experimentation with intra-element communication and bus architecture. Systems have ranged from several chips on a PCI board to server sized machines, but all suffer from a number of disadvantages:

(a) Systolic arrays consist of hundreds to thousands of processing elements, where each processing element may require thousands of logic elements. The resulting systems are large (as measured in silicon area or number of chips), costly, and power hungry. The preferred embodiment of the systolic processor detailed in U.S. Pat. Nos. 5,964,860 and 5,632,041 to Peterson (1999, 1997 respectively), for example, shows that the 16 processing elements which fit on a chip require a total of 400,000 transistors, and that multiple chips are likely needed for a working system.

(b) Communication between thousands of processing elements, control units, and possibly multiple chips greatly reduces the theoretical processing power of systolic arrays. For example, in the preferred embodiment section of U.S. Pat. No. 5,706,498 to Fujimiya, et. al. (1998) it is noted that compute time is greatly restricted by bus transactions between units.

(c) Systolic arrays require specialized languages, compilers, and a non-standard programming model to fully utilize their capabilities.

The linear shift register method of matching first presented in U.S. Pat. No. 5,724,253 to Skovira of IBM (1998) alleviates some of these problems but still has several disadvantages:

(d) The IBM system uses an encoding where more chemically similar nucleotides have a shorter Hamming distance between their constituent bits. Using this encoding, the system adds the result of every XOR nucleotide comparison in order to obtain a sum score quantifying the dissimilarity of a particular sequence alignment. Determining a match through a sequential addition of each nucleotide comparison takes much longer than performing a match determining operation in parallel, and means that compute-time scales linearly as the query size increases.

(e) Only one alignment between the genome and query sequence is checked during an iteration.

(f) Considerable memory bandwidth is used as a dissimilarity score is written to memory for every alignment checked.

BACKGROUND OF THE INVENTION— OBJECTS AND ADVANTAGES

Accordingly, the general object of the multiple alignment genome sequence matching processor is to provide a fast and accurate system and method suitable for searching a genomic data vector using a query DNA fragment. Such a system provides rapid search and query capabilities to large databases of genetic data, and accelerates the process of sequence assembly. Several other general objects and advantages of the present invention are:

(a) to provide a system which has a small hardware footprint, and is therefore both highly computationally-efficient and low power;

(b) to provide a system that by design requires very little communication between its requisite elements, and may therefore operate at higher speeds;

(c) to provide a system that uses a conventional programming model and computer architecture, including a conventional memory subsystem architecture, in order to reduce cost and improve programmability;

(d) to perform a comparison between multiple nucleotides from the genome and query sequences in parallel to increase speed over a sequential comparison of nucleotides;

(e) to perform a comparison between multiple alignments of the genome and query sequences in parallel to increase speed over a system which can check only one alignment at a time; and (f) to write only the location of exact matching alignments to memory, in order to reduce bandwidth requirements.

Further objects and advantages are to provide a mechanism to reduce memory fetch requirements thereby speeding compute time; to provide a system that exploits the nature of genetic data to rapidly find small exact matches (called hits), one of the core computational tasks of many bioinformatics algorithms; and to provide a system capable of performing DNA sequence assembly an estimated one thousand times faster than a conventional general purpose computer using the pair-wise comparison of fragment reads. Still further objects and advantages will become apparent from a consideration of the subsequent description and drawings.

SUMMARY

The multiple alignment genome sequence matching processor slides a sequence to be searched, such as a genome, past a query sequence, such as a DNA fragment, via shift registers. In parallel, multiple alignments between search and query sequences are compared. As each alignment consists of many elements (characters), the parallel matching process is highly accelerated over sequential element-by-element, single-alignment comparison. Individual element comparisons are made using equivalence operators, such as XNOR logic gates. The results of individual element comparisons are then consolidated into a single signal: "hit" or "miss," indicating whether all the elements for the particular alignment under test matched or not. After comparison, the search sequence is shifted by a number of elements equal to the number of parallel alignments compared, and the process repeats. An additional shifting prefetch buffer increases memory efficiency by alleviating the need to fetch data every cycle.

According to one feature of the invention, each element is represented by a digital value assigned such that complementary DNA nucleotides receive complementary codes. This provides the option for XOR matching of complementary sequences or XNOR equivalence matching of identical sequences.

According to another feature of the invention, the match length between the data and query vectors can be varied dynamically.

DRAWINGS—FIGURES

FIG. 1 illustrates a two-way alignment sequence matching processor according to the present invention.

Figure 2:
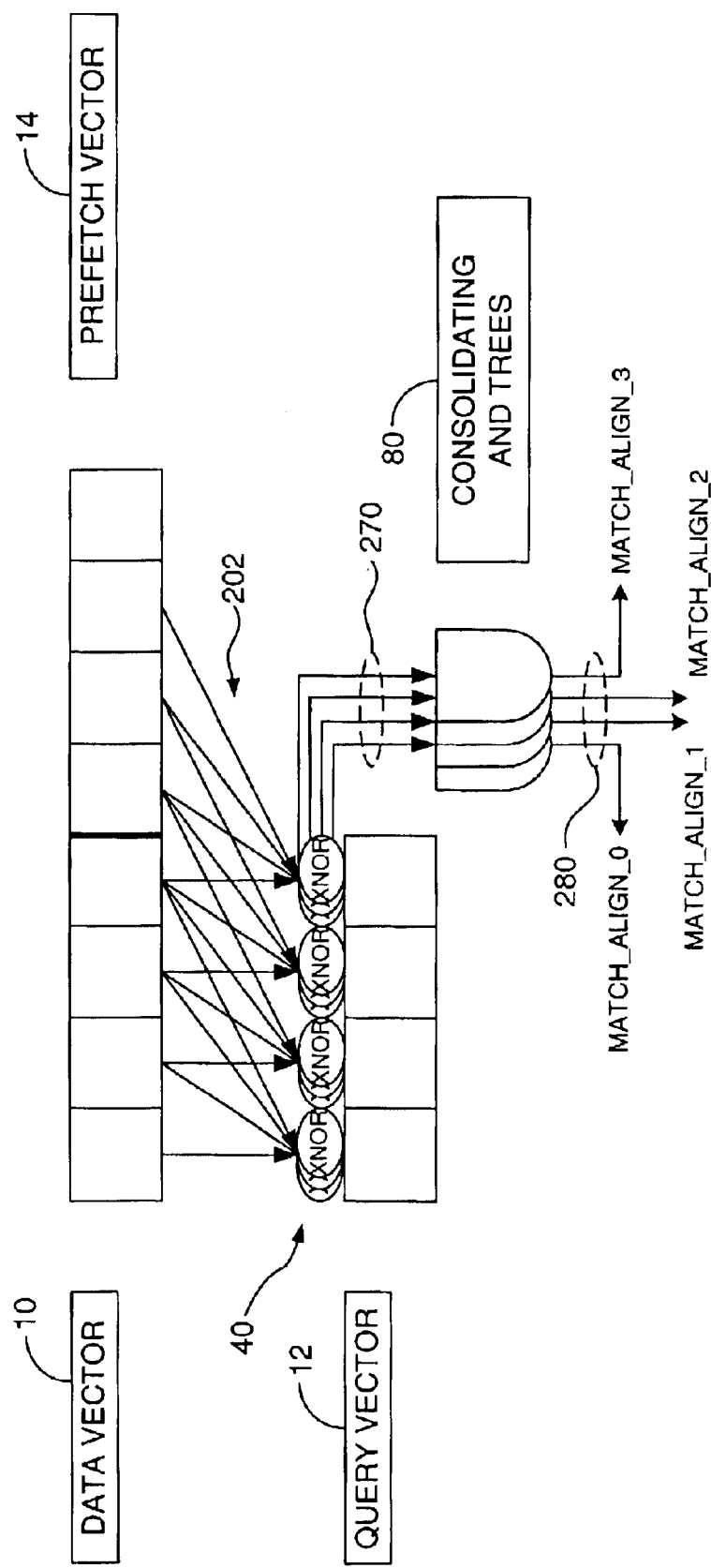

FIG. 2 details the cross-comparison mechanism for a four-way alignment sequence matching processor.

Figure 3:
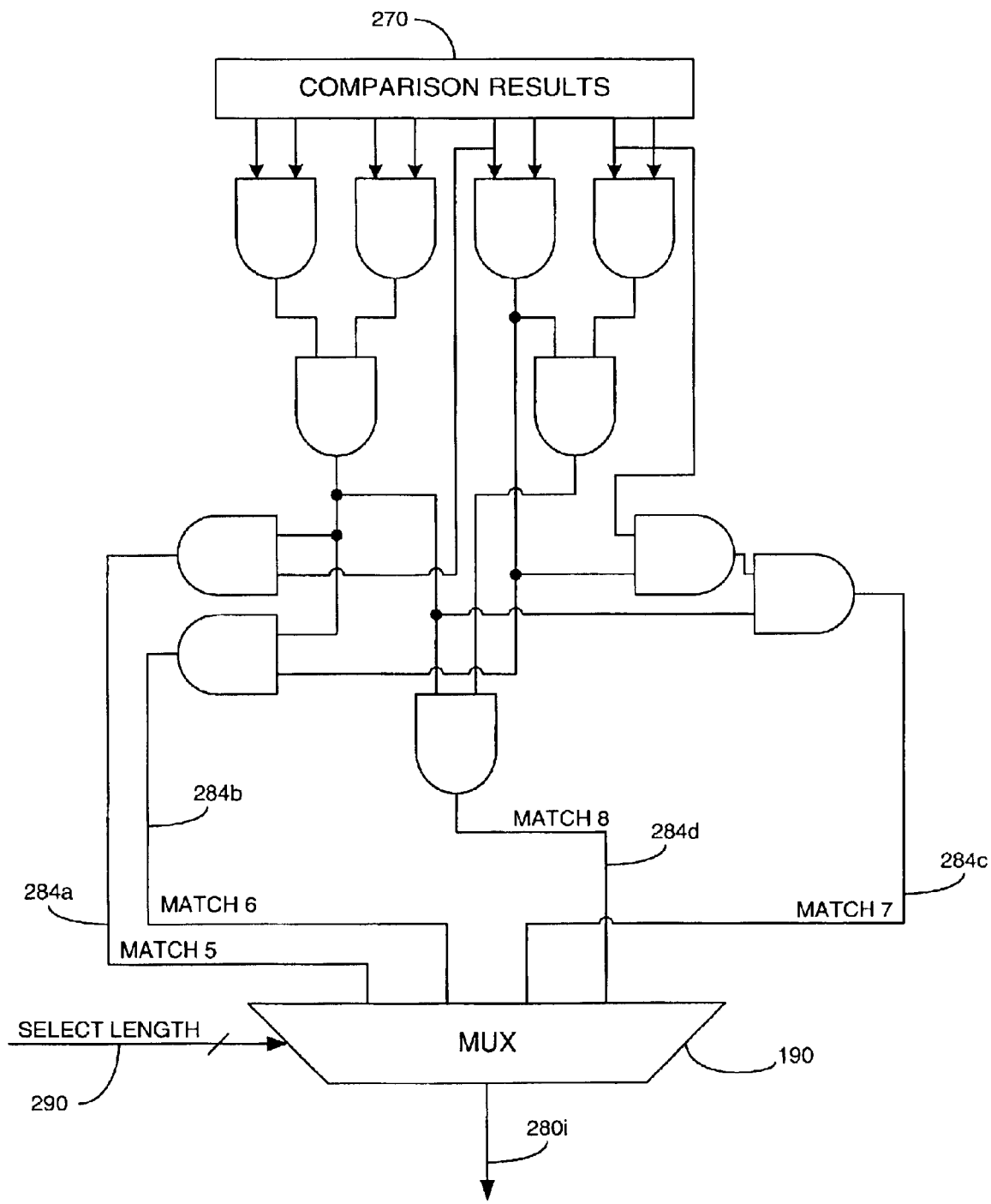

FIG. 3 details an extension to consolidating AND tree introduced in FIG. 1 which allows the match length between the data and query vectors to vary.

Figure 4B:
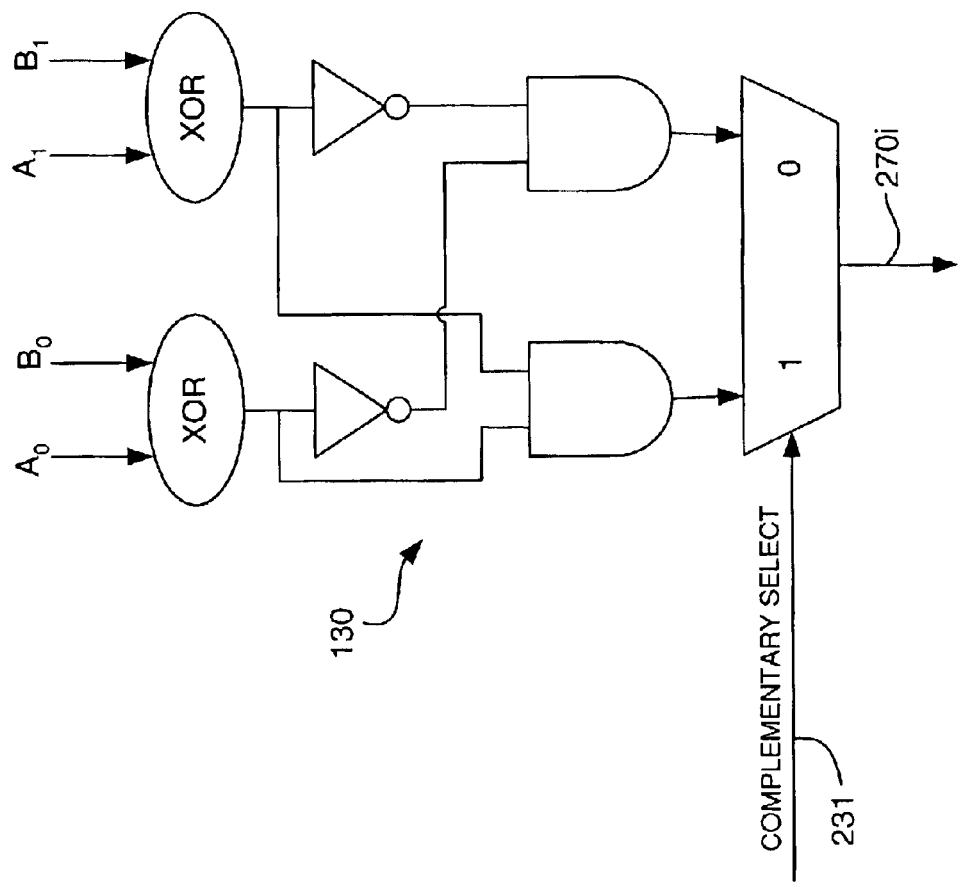
Figure 4A:
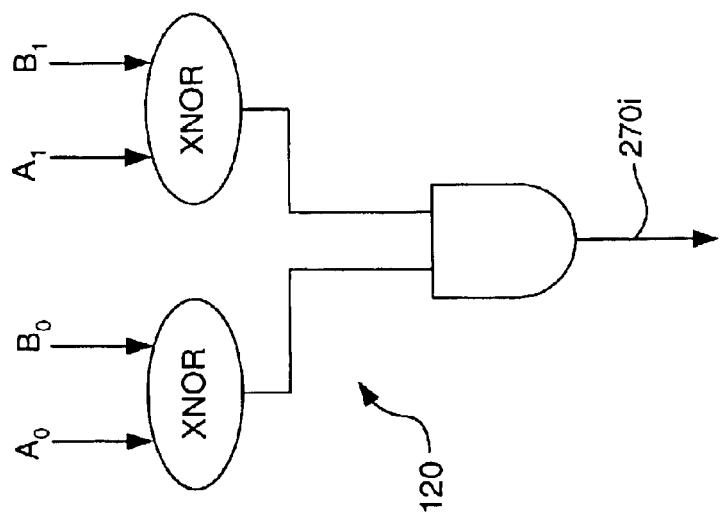

FIG. 4A details the logic gate implementation of an equivalence operator.

FIG. 4B details the logic gate implementation of an equivalence-complementary combined operator.

FIGS. 5A, 5B, and 5C show a time series operational interaction between the data and prefetch vectors.

DRAWINGS—REFERENCE NUMERALS

10 Data vector
12 Query vector
14 Prefetch Vector
20a–d: Alignment 0 equivalence operators
22 Alignment 0 comparison block
30a–d: Alignment 1 equivalence operators
32 Alignment 1 comparison block
40 Comparison engine
80 Consolidating AND trees
80a Alignment 0 consolidating AND tree
80b Alignment 1 consolidating AND tree
120 XNOR equivalence operator schematic
130 XOR/XNOR complementary/equivalence combined operator schematic
150 Choose alignment block
160 Incrementing genome index
190 AND tree mux for selecting variable match length
202 Cross-comparison wiring network
230 Select line for complementary or equivalence matching
240 Next input elements
250 Write enable signal
252 Least significant bits of match index
260 Index output bus
262 Most significant bits of match index
270 Results of element comparisons
270a Output bus for alignment 0 element comparisons
270b Output bus for alignment 1 element comparisons
270i Individual element comparison result
280 Results from AND tree consolidation
280a Result from alignment 0 AND tree
280b Result from alignment 1 AND tree
280i Individual result from an AND tree
284a Matched five elements output
284b Matched six elements output
284c Matched seven elements output
284d Matched eight elements output
290 Select line for variable length matching Detailed Description—Preferred Embodiment—FIGS. 1, 2, and 4A A preferred embodiment of the multiple alignment genome sequence matching processor is illustrated in FIG. 1. A data vector 10 comprising of K shift memory elements contains a portion of a sequence such as a genome. While only four such elements are shown for purpose of illustration (K=4), in practice, the number of elements may be much larger. Each element or box in the data vector represents one data character, such as a nucleotide. Since there are only four nucleotides in DNA—Adenine, Thiamine, Guanine, and Cytosine—each element comprises two bits.

A prefetch vector 14 comprising of shift memory elements is connected to data vector 10. The connection is such that the adjacent portion of the genome residing in the prefetch vector may be shifted into the data vector. Each element in the prefetch vector represents one data character, such as a nucleotide. The prefetch vector in the preferred embodiment is chosen to have the same number of elements as the data vector, though this number may vary.

A query vector 12 consisting of K memory elements contains a portion of a different sequence such as a DNA fragment. Again, each element represents a character such as a nucleotide. The query vector in the preferred embodiment is chosen to have the same number of elements as the data vector, though this number may vary.

A comparison engine 40 connects data vector 10 and prefetch vector 14 to query vector 12 using a cross-comparison wiring network 202. The data and prefetch vectors collectively hold a contiguous portion of the sequence to be searched, while the query vector holds the sequence fragment acting as the query in that search. In the preferred embodiment, the comparison engine tests multiple alignments between the genome and the fragment for equivalence. Although only two such alignments, alignment 0 and alignment 1, are drawn in FIG. 1 for purpose of illustration, the number of alignments tested may vary.

The comparison between genome and query fragment for alignment 0 is performed by an alignment 0 comparison block 22 which consists of exclusive NOR (XNOR) logic gates 20a, 20b, 20c, and 20d. The output of an XNOR logic gate is asserted when its inputs match exactly. For this reason, XNOR is also known as the equivalence gate or equivalence operator. As a nucleotide can be represented in 2 bits, XNORs with 2-bit inputs are used for the comparison. In practice, these may be achieved through the logical AND of two 1-bit input XNORs as illustrated in FIG. 4A.

A parallel comparison on alignment 0 is performed where XNOR gate 20a compares the first nucleotide in genome data vector 10 with the first nucleotide in query vector 12, XNOR gate 20b compares the second nucleotide in genome data vector 10 with the second nucleotide in query vector 12, XNOR gate 20c compares the third nucleotide in genome data vector 10 with the third nucleotide in query vector 12, and XNOR gate 20d compares the fourth nucleotide in genome data vector 10 with the fourth nucleotide in query vector 12. In total, the alignment 0 comparison consists of a parallel comparison of elements 0 to 3 in the data vector to the corresponding elements 0 to 3 in the query vector.

The comparison between genome and query fragment for alignment 1 is performed by an alignment 1 comparison block 32 which consists of exclusive NOR (XNOR) logic gates 30a, 30b, 30c, and 30d. In parallel, XNOR gate 30a compares the second nucleotide in genome data vector 10 with the first nucleotide in query vector 12, XNOR gate 30b compares the third nucleotide in genome data vector 10 with the second nucleotide in query vector 12, XNOR gate 30c compares the fourth nucleotide in genome data vector 10 with the third nucleotide in query vector 12, and XNOR gate 30d compares the first nucleotide in genome prefetch vector 14 with the fourth nucleotide in query vector 12. In total, the alignment 1 comparison consists of a parallel comparison of elements 1 to 3 in the data vector and element 0 in the prefetch vector to the corresponding elements 0 to 3 in the query vector.

In generalized terms, for K-element wide data, prefetch, and query vectors, an alignment P comparison consists of a parallel comparison via XNOR gates of elements P to (K−1) of data vector 10 and the first P elements of prefetch vector 14 to the corresponding elements 0 to (K−1) in query vector 12. This generalization is restricted to the condition that P is less than or equal to K.

The result of an individual XNOR comparison will be a binary 1 or 0 indicating either the equivalence of the nucleotides or their dissimilarity respectively. Individual element comparison results 270 from comparison engine 40 are sent to consolidating AND trees 80. The individual element results from the alignment 0 comparison block are sent down a bus 270a to alignment 0 consolidating AND tree 80a. The individual element results from the alignment 1 comparison block are sent down a bus 270b to alignment 1 consolidating AND tree 80b.

The consolidating AND trees perform a logical AND operation on their inputs. Hence, the output of a binary 1 from an AND tree indicates an exact match between multiple nucleotides. If the output of the alignment 0 consolidating AND is asserted, all elements of alignment 0 matched. If the output of the alignment 1 consolidating AND is asserted, all elements of alignment 1 matched.

AND tree outputs 280 are fed into choose alignment block 150. The choose alignment block asserts a write enable signal 250 of external memory storage if any of the AND tree outputs are asserted, indicating a match or "hit" for some alignment. The choose alignment block also outputs the alignment number of the match to least significant bits 252 of index bus 260.

An incrementing index 160 increments by P, the number of simultaneous alignments checked by comparison engine 40, in order to keep track of the current location in the genome. Each time the genome residing in data vector 10 and prefetch vector 14 is shifted, the index increments. The incrementing index outputs most significant digits 262 of match index to index bus 260. The index bus 260 is written as data into external memory when write enable signal 250 is asserted. Hence, when a match between the genome and query is found, the location where the match occurred is written to memory.

In general, it is not actually necessary to increment by P for each shift of the genome. Rather, if P is a power of 2, an index which increments by 1 may be substituted. This index will supply the upper $\log_2(P)$ to P most significant bits to index bus 260 while choose alignment block 150 supplies the remaining least significant bits based on which alignment produced the match.

FIG. 2 illustrates the cross-comparison mechanism for a four-way alignment sequence matching system for purpose of clarification. Here, comparison engine 40 contains four sets of XNOR gates (shown overlapping to emphasize the cross-comparison wiring), where each set compares a different alignment. Set 0 compares elements 0 to 3 of data vector 10 to the corresponding elements 0 to 3 of query vector 12. Set 1 compares elements 1 to 3 of data vector 10 and element 0 of prefetch vector 14 to the corresponding elements 0 to 3 of query vector 12. Set 2 compares elements 2 to 3 of data vector 10 and elements 0 to 1 of prefetch vector 14 to the corresponding elements 0 to 3 of query vector 12. Set 3 compares element 3 of data vector 10 and elements 0 to 2 of prefetch vector 14 to the corresponding elements 0 to 3 of query vector 12. Wiring network 202 which permits such cross-comparison is the primary purpose of this illustration.

Since four alignments were checked, four consolidating AND trees 80 will be required. These AND trees will consolidate the element comparisons into output signals 280 indicating whether or not a match occurred for each alignment.

Detailed Description—FIGS. 3 and 4B—Additional Features

FIG. 3 details an extension to consolidating AND tree introduced in FIG. 1 which allows the match length between the data and query vectors to vary. This is an important extension feature to the preferred embodiment as it adds flexibility to an otherwise hardwired and static match length. FIG. 3 illustrates how such flexibility could be achieved for an embodiment which compares 8 nucleotides in parallel, and therefore produces 8 bits of comparison results 280. By breaking the monolithic 8-bit AND gate into a tree of 2-bit AND gates, the outputs of those gates can be tapped to determine if a match occurred for less than 8 elements.

For example, match 5 output 284a will be asserted when the first five comparison result bits are asserted. This indicates a match between the first five elements compared. Match 6 output 284b will be asserted when the first six elements compared are equivalent. Similarly, match 7 output 284c and match 8 output 284d will be asserted if the first 7 and 8 elements respectively are equivalent. A select line 290 is used with a multiplexor 190 to choose the desired match length from among the outputs generated. An individual AND tree result 280i is then sent to the choose alignment block as previously illustrated.

FIG. 4A shows the schematic of an equivalence operator 120 (also known as an XNOR gate) which has 2-bit inputs A and B. Functionally, it can be seen that a multi-bit equivalence operation is simply the logical AND of multiple single-bit equivalence operations.

FIG. 4B shows the logic gate schematic for a combination equivalence-complementary match operator 130 with 2-bit inputs. The 2-bit XNOR gate can be implemented by inverting the outputs of two XOR gates and performing a logical AND. A 2-bit complementary match operation can be implemented through the logical AND of the XOR gate outputs. Once generated, select line 230 can send either the equivalence of complementary match outputs as a comparison element result 270i.

When complementary data elements are given bit-wise complementary codes as shown in table 1 below, this combined unit allows for either element complementary or element equivalence matching between genome and fragment sequences. This is important, as DNA is made of complementary nucleotide pairs arranged in a double helix. Since either side of that helix may have been sequenced, the genome database being queried may store the complement of the query in question. The ability to search in either mode is therefore desirable.

TABLE 1

Nucleotide base pair encoding. Complementary pairs are given complementary codes.

| DATA | QUERY | EQUIVALENCE RESULT | COMPLEMENTARY RESULT |
|---|---|---|---|
| A = 00 | 00 | 1 | 0 |
|  | 01 | 0 | 0 |
|  | 10 | 0 | 0 |
|  | 11 | 0 | 1 |
| C = 01 | 00 | 0 | 0 |
|  | 01 | 1 | 0 |
|  | 10 | 0 | 1 |
|  | 11 | 0 | 0 |
| G = 10 | 00 | 0 | 0 |
|  | 01 | 0 | 1 |
|  | 10 | 1 | 0 |
|  | 11 | 0 | 0 |
| T = 11 | 00 | 0 | 1 |
|  | 01 | 0 | 0 |
|  | 10 | 0 | 0 |
|  | 11 | 1 | 0 |

Detailed Description—Alternative Embodiments

The multiple alignment genome sequence matching processor may be pipelined (not shown) such that the results from the individual nucleotide comparisons are immediately buffered. The contents of the data and prefetch vectors can then be shifted and compared in the next cycle, while the consolidating AND trees operate on buffered results from the last round of comparisons. Pipelining has the possibility of speeding the processor considerably, as the compare, AND, choose alignment critical path is eliminated. The new critical path should reside in either the XNOR comparison gate or the consolidating AND, both of which are simple and therefore fast hardware operations.

Operation—FIGS. 1 and 5

Variables Used

P—the number of simultaneous alignments tested.

K—the number of elements checked by each alignment.

To use the preferred embodiment of the multiple alignment genome sequence matching processor, a genome segment is fetched from memory by an external controller and placed in data vector 10. An adjacent and contiguous segment of the genome is placed into prefetch vector 14. A DNA fragment constituting a search or query pattern against the genome is placed into query vector 12.

In theory, there is no limitation on the size of these vectors. In practice, the size is dictated largely by the fetch size of the memory architecture. In a conventional memory architecture, a 32-bit word fetch is common. Since the four letters of DNA—ATGC—can be encoded in only two bits, this 32-bit word fetch contains K=16 nucleotides. This is close to the match length of interest for many bioinformatics algorithms, making the sequence matching processor a good fit for conventional memory architecture. The preferred encoding of the nucleotides is as shown in table 1, where complementary nucleotide pairs, A-T and G-C, are given complementary bit codes.

During the initialization process, incrementing index 160 which keeps track of the current position in the genome is zeroed.

After data has been initially placed in the K-element data, prefetch, and query vectors, comparison can begin. Comparison engine 40 uses P sets of XNOR gates to check P alignments of K elements each in parallel. This leads to a total of K×P nucleotide comparisons per cycle, and is therefore much faster than a sequential comparison.

Results of the individual element comparisons 270 are sent along buses to consolidating AND trees 80. The output of each AND tree determines if there is a match for the associated alignment. A match between the genome and query vectors is an exact match of K nucleotides. In biology, this is called a K-mer "hit." Matching small segments—that is, finding "hits"—allows for the deletions, insertions, substitutions, and errors which are prevalent in DNA. For example, an insertion may be flanked on both sides by a hit. The offset between the locations of these hits gives the size of that insertion. The same is true of substitutions and deletions. Matching small regions of DNA is the core computational task of many genetic processing algorithms. These hits are then combined, weighted, and correlated for higher level genetic analysis.

AND tree outputs 280 are fed into choose alignment block 150. The choose alignment block asserts write enable signal 250 of external memory storage if any of the AND tree outputs are asserted, indicating a match or "hit" for some alignment. The choose alignment block also outputs the alignment number of the match to least significant bits 252 of index bus 260.

For example, if AND align 180a introduced in FIG. 1 indicated a hit, least significant index bit 252 would be set to a binary 1. In an embodiment which compared four alignments, if the alignment 3 matched, the least significant index bits would be set to 11, the binary equivalent of 3. In order to facilitate the conversion of alignment number to its binary equivalent, the number of simultaneous alignments P checked by comparison engine 40 should be a power of two.

An incrementor 160 keeps track of the current location in the genome being searched. Each time the genome residing in data vector 10 and prefetch vector 14 is shifted, the index increments. This incrementor is used to supply the most significant bits of a match location to index bus 260, the least significant bits being determined by the choose alignment block. When a match occurs, the value of index bus 260 specifies the location (index) of that match within the genome. This value is written into external memory when write enable signal 250 is asserted.

When comparison engine 40 has completed its element comparisons, data vector 10 and prefetch vector 14 are shifted to the left by P elements. During a shift, elements from the left side of the prefetch vector are moved into the right side of the data vector. This ensures that the data vector is always filled with valid data elements. The result of this arrangement is that a memory fetch is needed only every K/P cycles in order to ensure that the elements being compared are valid.

This point is illustrated in detail in the time series FIGS. 5A, 5B, and 5C. Here, the data and prefetch vectors are filled with contiguous alphanumeric characters for ease of example.

FIG. 5A shows the data and prefetch vectors filled with characters A through H. Also shown is cross-comparison wiring network 202 which leads to the comparison engine. Each of the elements connected to this wiring network must be valid at all times for a valid comparison between genome and fragment to be made. A blank box will be used to indicate an invalid element position.

FIG. 5B shows the data and prefetch vectors after a cycle of operation. Here, the contents of the vectors have been shifted to the left by two elements (i.e. the number of alignments checked in this embodiment). At this time, the rightmost two elements of the prefetch vector are invalid. However, since all of the elements connected to the comparison engine are valid, no new data needs to be input from memory. During this time, next input signals 240 may either be waiting or in the process of being fetched.

FIG. 5C shows the data and prefetch vectors after another cycle of operation. The contents of the vectors have again been shifted to the left by two elements. New elements have been accepted into the prefetch vector to avoid an invalid comparison. The acceptance of new values into the prefetch vector can be triggered by a counter or external signal.

It can be seen from this example where K=4 and P=2, that a memory fetch is required every K/P=2 cycles so that all data being compared is valid. By alleviating the need to fetch every cycle, the system increases memory efficiency, a crucial concern in conventional computing where memory is often the primary bottleneck.

The overall operation of the sequence matching processor is to find exact matches of predetermined length between a search sequence and query sequence through a shift and compare loop. At each shift position, multiple alignments between search and query sequence are checked in parallel, allowing accelerated search speed.

If the match length defined by hardware is shorter than the desired match length, the matching processor may be operated as follows. Once a match of length K between the search and query sequences has been found, the adjacent sections of both sequences are loaded into the data and query vectors respectively. The matching processor operates as usual, indicating a hit (match) or miss for this new data. In the case of a hit at this location, the total match length (inclusive of the prior match) now exceeds K. This procedure may be repeated and used with the variable match length feature to provide for any match length desired.

Conclusion, Ramifications, and Scope

Thus the multiple alignment genome sequence matching processor meets the requisite objects and advantages previously put forth:

a) The multiple alignment genome sequence matching processor consists of several registers, K×P XNOR gates, several AND gates, an incrementer, and other relatively simple logic. This small design means a small silicon footprint and low power consumption. Both of these lead to lower costs and better integration in a system-on-a-chip or portable-device application. An 8 nucleotide, two-way alignment processor has been constructed using only about 4000 transistors (Aaron Patzer. "Highly Parallel DNA Sequence Matching and Alignment Processor." IEEE DDECS Conf., Apr. 17–19, 2002.)

b) Due to its linear shift-comparison mechanism, the multiple alignment genome sequence matching processor has little communication overhead compared to a systolic array which must coordinate the activities of many discrete processing elements.

c) The multiple alignment genome sequence matching processor can be constructed for use with a conventional memory system which supports 32-bit word fetches, each word fetch containing 16 coded nucleotides. This is close to the match length of interest for many bioinformatics algorithms, making the sequence matching processor a good fit for conventional memory architecture. Programming the sequence matching processor requires placing data into the data, prefetch, and query vectors. This can be accomplished either by a microprocessor mtspr (move-to special purpose register) command, or through a simple memory controller.

d) A 2K-bit vector with K XNOR equivalence gates allows K simultaneous nucleotide comparisons to be made for each alignment. This use of parallelism increases speed significantly over systems and methods which compare nucleotides sequentially.

e) A novel cross comparison method allows P alignments between the genome and query sequences to be checked in parallel. Since each alignment compares K elements, a total of K×P nucleotides are compared every cycle. This is faster than comparing a single alignment each cycle, and much faster than a sequential, single element comparison method.

f) Write bandwidth is decreased as a value is only written to memory when there is an exact match (hit) between the genome and query sequences.

g) A prefetch buffer eliminates the need for fetching data every cycle.

h) Pipelining combined with a short critical path allows high clock speeds, thereby delivering an increased number of nucleotide comparisons per second.

Although the description above contains many specificities, these should not be construed as limiting the scope of the multiple alignment genome sequence matching processor, but as merely providing illustrations of some of the presently preferred embodiments. For example, the size of the genome and query fragment vectors can vary according to implementation; the number of simultaneous alignments checked can vary; a variety of incrementing blocks may be used to keep track of the current position in the genome; strings with an alphabet greater than four letters can be matched instead of genomes, etc.

Thus the scope of the invention should be determined by the appended claims and their legal equivalents, rather than by the examples given above.

I claim:

1. A method of multiple alignment sequence matching comprising:
   (a) providing a first storage vector which is able to store a first series of digital sequence elements,
   (b) providing a means for shifting the contents of said first storage vector one or more elements,
   (c) providing a second storage vector which is able to store a second series of digital sequence elements,
   (d) providing a comparison engine which is operatively connected between said first storage vector and said second storage vector which will:
      (1) provide a plurality of comparison sets, said comparison sets providing a plurality of equivalence operators,
      (2) provide a means of testing the bit-wise equivalence of an element from said first storage vector to an element from said second storage vector via said equivalence operators,
      (3) provide the parallel operation of said comparison sets of said equivalence operators so that the equivalence of a plurality of elements in a plurality of possible alignments between said first storage vector and said second storage is tested,
   (e) providing a plurality of logical AND operators, each of which can take a plurality of inputs,
   (f) providing a means for moving the outputs of said equivalence operators in said comparison sets to the inputs of said logical AND operators,
   (g) whereby the output of said logical AND operator is asserted if an exact match between all elements of the particular alignment tested by the associated comparison set occurs or is not asserted if one or more elements of that alignment does not match,
   (h) providing a means for triggering the first storage vector to shift its elements by a predetermined amount with respect to the second storage vector,
   (i) providing a means for triggering the first storage vector to accept additional elements from said first series of digital sequence elements,
   whereby said first series of digital sequence elements represents the sequence to be searched, and
   whereby said second series of digital sequence elements represents the query sequence to be matched against the first sequence, and
   whereby the method can be used to look for exact matches of predetermined length between the search and query sequences by testing the equivalence of multiple elements from multiple alignments in parallel to improve speed over a sequential, element-by-element matching.

2. A multiple alignment sequence matching processor comprising:
   (a) a first storage vector which is able to store a first series of digital sequence elements,
   (b) a means for shifting the contents of said first storage vector one or more elements,
   (c) a second storage vector which is able to store a second series of digital sequence elements,
   (d) a comparison engine which is operatively connected between said first storage vector and said second storage vector comprising:
      (1) a plurality of comparison sets,
      (2) said comparison sets each operatively connected between a like number of elements from said first storage vector and said second storage vector,
      (3) said comparison sets comprising a plurality of equivalence operators,
      (4) said plurity of equivalence operators operatively connected between the individual sequence elements of said first storage vector and said second storage vector,
      (5) said equivalence operator providing a means of testing the bit-wise equivalence of an element from said first storage vector to an element from said second storage vector,
      (6) said comparison sets of said equivalence operators acting in parallel to provide a means of testing in parallel a plurality of element equivalences between a plurality of possible alignments between said first storage vector and said second storage,
   (e) a plurality of logical AND structures, each of which has a plurality of inputs,
   (f) said comparison sets each operatively connected to a unique said logical AND structure such that each said input to said logical AND structure is the output of said equivalence operators in said comparison set,
   (g) whereby the output of said logical AND structure is asserted if an exact match between all elements of the particular alignment tested by the connected comparison set occurs or is not asserted if one or more elements of that alignment does not match,
   (h) means for triggering said first storage vector to shift its elements by a predetermined amount with respect to said second storage vector,
   (i) means for triggering said first storage vector to accept additional elements from said first series of digital sequence elements,
   whereby said first series of digital sequence elements represents the sequence to be searched, and
   whereby said second series of digital sequence elements represents the query sequence to be matched against the search sequence, and
   whereby the system can be used to look for exact matches of predetermined length between the search and query sequences by testing the equivalence of multiple elements from multiple alignments in parallel to improve speed over a sequential, element-by-element matching.

3. The multiple alignment sequence matching processor of claim 2 wherein said means for shifting contents of said first storage vector comprises a shift register.

4. The multiple alignment sequence matching processor of claim 2 further including a means for keeping track of position within said digital sequence of elements during operation of the processor,
   whereby upon detecting a match, this position can be output to record the location of that match.

5. The multiple alignment sequence matching processor of claim 2 further including:
   (a) a means of determining if any of said logical AND structures asserted their outputs to indicate a match, and
   (b) a means of determining which of said logical AND structures if any asserted their outputs, whereby a write enable can be asserted to send the location of a match to external memory and the least significant bits of that match location may be determined.

6. The multiple alignment sequence matching processor of claim 2 wherein said first storage vector is logically divided into a data storage vector and a prefetch storage vector, said prefetch storage vector having a means for shifting said first series of digital sequence elements into said data storage vector, whereby said means for shifting allows said data storage vector to remain filled with valid sequence elements so that valid comparisons are made, whereby said prefetch storage vector alleviates the need for additional sequence elements to be input every shift and compare cycle, thereby reducing memory bandwidth.

7. The multiple alignment sequence matching processor of claim 2 wherein said logical AND structure having K inputs contiguously numbered 0 through K−1 is decomposed into tree with a like number of inputs comprising a plurality of smaller logic structures each having fewer than K inputs, said smaller logic structures being operatively connected to form a plurality of tree outputs, and each of said tree outputs being the logical AND of inputs 0 through L, L being less than K.

8. The multiple alignment sequence matching processor of claim 7 wherein said tree outputs are operatively connected to a multiplexor, whereby the match length between the search and query sequences can be varied by selecting the tree output indicative of the desired length via said multiplexor.

9. The multiple alignment sequence matching processor of claim 2 wherein complementary sequence elements are represented by bit-complementary codes.

10. The multiple alignment sequence matching processor of claim 9 further including:

(a) a plurality of inversion operators each operatively connected to said equivalence operators such that the combination operator tests exact bit-wise dissimilarity, (b) a plurality of multiplexors with a common select line each operatively connected to the output of the equivalence operator and the output of the combination operator, whereby the system can be used to look for exact matches of a predetermined length between complementary elements through an inverse equivalence test or exclusive ORing of multiple elements from multiple alignments in parallel, thereby improving speed over a sequential, element-by-element complementary matching.

11. The multiple alignment sequence matching processor of claim 2 wherein (a) said plurality of equivalence operators comprise exclusive NOR (XNOR) logic gates which have a plurality of inputs and a single output, (b) said single output indicating the equivalence of sequence elements through a logical 1 and dissimilarity of sequence elements through a logical 0, (c) said comparisons sets of said equivalence operators operatively connected to provide a plurality of cross-comparisons for a plurality of possible alignments between said first storage vector and said second storage vector, (d) said means for triggering the first storage vector to shift its elements comprising a predetermined digital shift signal, (e) said means for triggering the first storage vector to accept additional elements from said first series of digital sequence elements comprising a predetermined digital accept signal, and further including (f) a digital incrementer operatively connected to said predetermined digital shift signal which keeps track of the current position or index within said first series of digital sequence elements, (g) a choose alignment block operatively connected to the output of said logical AND structures which asserts a write enable signal if any output of said logical AND structures is asserted, whereby a digital hardware system for finding exact matches of predetermined length between a search sequence and query sequence is performed through a shift and compare loop, whereby multiple potential alignments between search and query sequence are checked in parallel at each shift position, whereby a system exceeding the speed of sequential or single alignment comparison is established.

* * * * *